(12) United States Patent
Khair et al.

(10) Patent No.: US 11,471,283 B2
(45) Date of Patent: Oct. 18, 2022

(54) SYSTEMS AND METHODS FOR TREATING PRESERVED EJECTION FRACTION CONDITIONS

(71) Applicant: Regents of the University of Minnesota, Minneapolis, MN (US)

(72) Inventors: Andrew Khair, Eden Prairie, MN (US); Julianna Abel, Minneapolis, MN (US); Adam Lin Choe, Coon Rapids, MN (US); Thomas O. Viker, New Brighton, MN (US); Henry Koon, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 688 days.

(21) Appl. No.: 15/899,174

(22) Filed: Feb. 19, 2018

(65) Prior Publication Data

US 2018/0235760 A1    Aug. 23, 2018

Related U.S. Application Data

(60) Provisional application No. 62/460,377, filed on Feb. 17, 2017.

(51) Int. Cl.
*A61F 2/24* (2006.01)
*A61B 17/00* (2006.01)
*A61F 2/90* (2013.01)

(52) U.S. Cl.
CPC .. *A61F 2/2487* (2013.01); *A61B 2017/00243* (2013.01); *A61B 2017/00592* (2013.01); *A61F 2/90* (2013.01); *A61F 2220/0075* (2013.01); *A61F 2230/0004* (2013.01)

(58) Field of Classification Search
CPC .......... A61F 2/24; A61F 2/2487; A61M 29/00
See application file for complete search history.

(56) References Cited

U.S. PATENT DOCUMENTS

| | | | |
|---|---|---|---|
| 2004/0243170 A1* | 12/2004 | Suresh | A61F 2/2487 606/198 |
| 2012/0028003 A1* | 2/2012 | Abrams | B32B 7/12 428/196 |
| 2012/0130477 A1 | 5/2012 | Gessaroli | |
| 2018/0078328 A1 | 3/2018 | Rosenberg et al. | |

* cited by examiner

*Primary Examiner* — Matthew W Schall
(74) *Attorney, Agent, or Firm* — Patterson Thuente Pedersen, P.A.

(57) ABSTRACT

A device of a shape memory material configured to implement a predetermined level of expansion while allowing contraction and twist can be implemented in a portion of a vascular system, such as in the left ventricle of the heart of a patient suffering from heart failure with preserved ejection fraction.

21 Claims, 18 Drawing Sheets

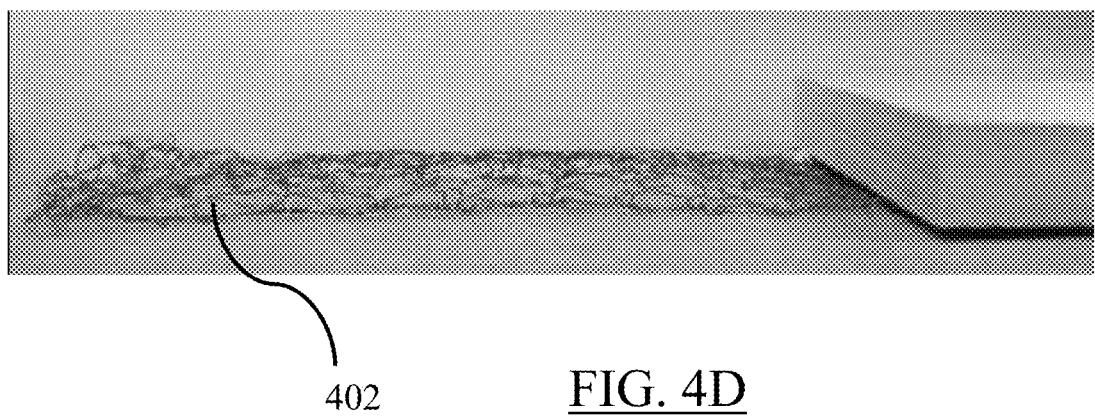
402  FIG. 4D
403  FIG. 4E

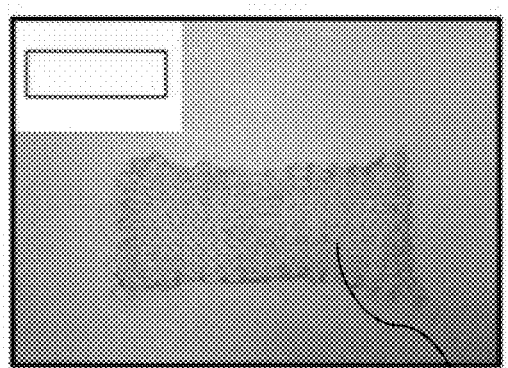
FIG. 5D   502
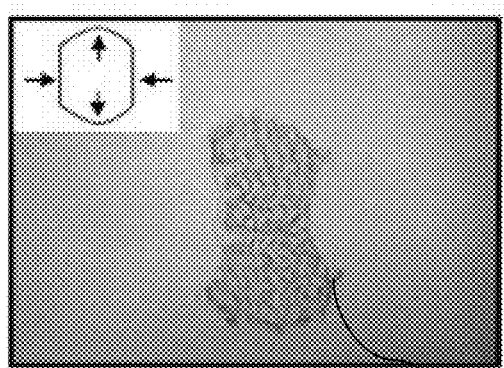
FIG. 5E   502'

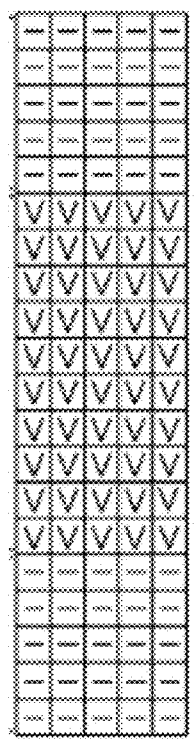 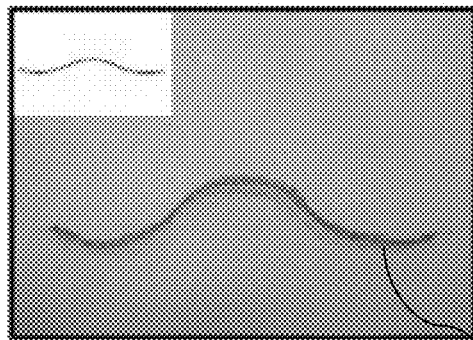 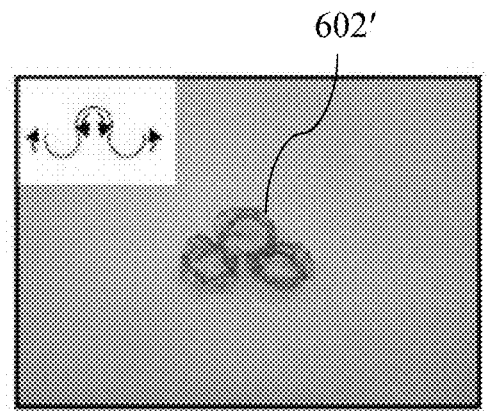
FIG. 6A   FIG. 6B   602   FIG. 6C

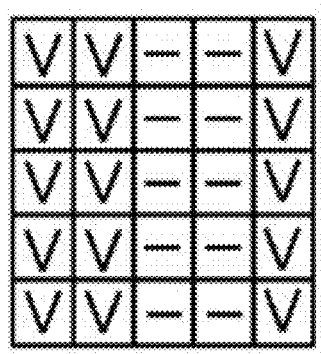
FIG. 7A
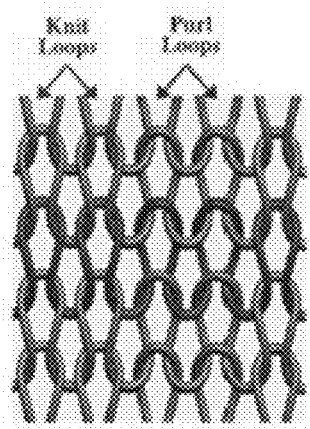
FIG. 7B
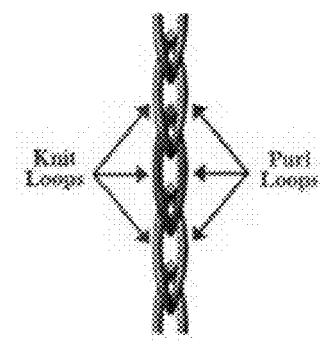
FIG. 7C
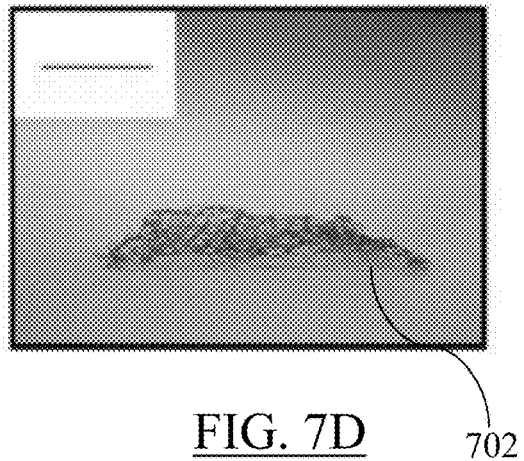
FIG. 7D 702
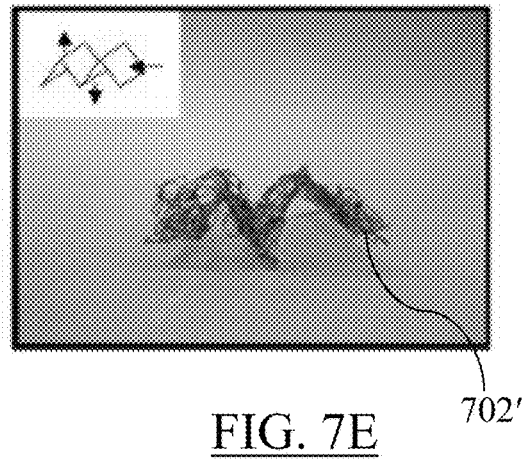
FIG. 7E 702'

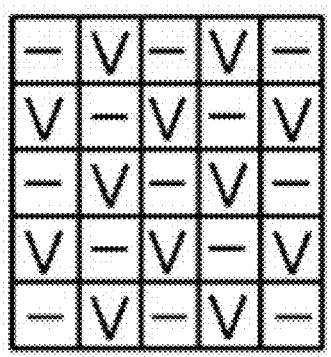
FIG. 8A
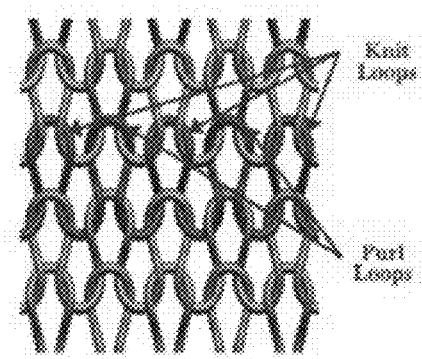
FIG. 8B
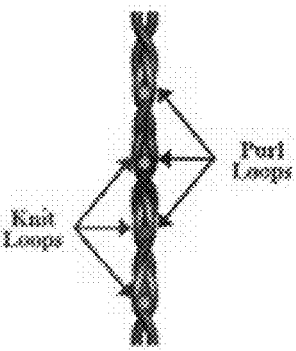
FIG. 8C
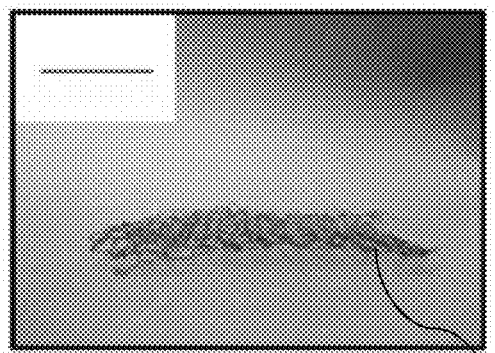
FIG. 8D  802
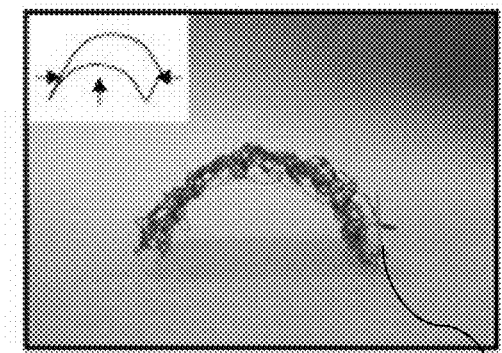
FIG. 8E  802'

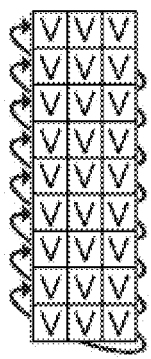
FIG. 12A
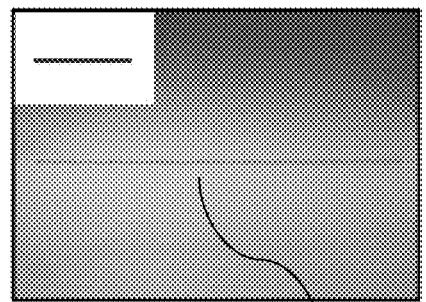
FIG. 12B  1202
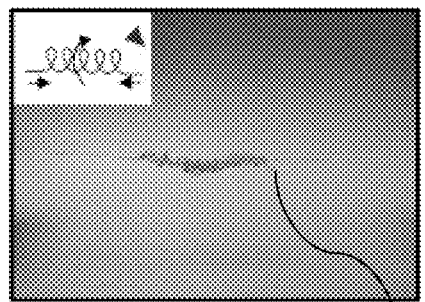
FIG. 12C  1202'

SYSTEMS AND METHODS FOR TREATING PRESERVED EJECTION FRACTION CONDITIONS

RELATED APPLICATION

The present application claims the benefit of U.S. Provisional Application No. 62/460,377 filed Feb. 17, 2017, which is hereby incorporated herein in its entirety by reference.

TECHNICAL FIELD

Embodiments relate to treatment of heart conditions, such as preserved ejection fraction, using an implantable device that can be delivered by catheter and that can provide radial outward force on a ventricle of the heart.

BACKGROUND

Heart failure with preserved ejection fraction (HFpEF) is a condition where the squeeze function of the heart is preserved yet clinical signs of heart failure are present. Almost 6 million people in the United States suffer from heart failure, with 40% of heart failure patients categorized as heart failure with HFpEF. In HFpEF, the left ventricle of the heart does not expand properly. Results of the left ventricle's inability to expand are a decrease in filling volume of the left ventricle, an increase in pressure in the left ventricle and left atrium, and pulmonary edema.

Epidemiologic studies suggest that the prevalence of and hospitalizations related to HFpEF are rising. There remains a lack of consensus on the basic pathophysiology and definition, classification, therapeutic targets, and goals for therapy for HFpEF. Even in those cases in which a person suffering from HFpEF is not hospitalized, exercise capacity and quality of life are reduced.

Additionally, there are no animal models ideally suitable for testing related to treating HFpEF. Changes leading to hospitalization and the differences between hospitalized versus outpatients are also incompletely understood. HFpEF can be affected by other systemic and pulmonary vascular abnormalities and may not be diagnosed in the absence of other indications of volume overload, such as kidney failure.

One known cause of HFpEF is left ventricular abnormalities. For example, abnormal ventricular arterial coupling, poor vasodilator reserve, chronotropic incompetence, coronary disease, microvascular dysfunction, and right ventricular dysfunction with or without coexisting pulmonary vascular disease can cause or compound HFpEF.

HFpEF prevalence is increasing, and patients suffering from HFPEF face impaired health status and an unabated high risk for adverse outcomes. The economic burden of HFpEF is substantial. To date, there is no approved therapy for these patients. Despite drug and device development for HFpEF, there is still a high post-discharge event rate and hospitalized rate for HFpEF patients. Currently, there are no clinical interventions available to HFpEF. While some pharmacological interventions showed early promise, these agents failed upon further clinical testing.

SUMMARY

Embodiments relate to a device comprising a plurality of knitted rows of a shape memory material configured to implement a predetermined level of contraction and twist. The device can be implemented in a portion of a vascular system, such as in the left ventricle of the heart of a patient suffering from heart failure with preserved ejection fraction.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 4D and 4E depict a martensite stage of the knitted shape memory material according to the pattern of FIGS. 4A-4C, respectively.

FIGS. 5D and 5E depict martensite and austenite stages of a knitted shape memory material according to the pattern of FIGS. 5A-5C, respectively.

FIGS. 6A-6C depict a grid of graphical symbols of a pattern, a martensite stage of the material in side view, and a austenite state of the material in side view, respectively.

FIGS. 7A, 7B, and 7C depict a grid of graphical symbols of a pattern, a top view of the pattern, and a side view of the pattern, respectively.

FIGS. 7D and 7E depict martensite and austenite stages of a knitted shape memory material according to the pattern of FIGS. 7A-7C, respectively.

FIGS. 8A, 8B, and 8C depict a grid of graphical symbols of a pattern, a top view of the pattern, and a side view of the pattern, respectively.

FIGS. 8D and 8E depict martensite and austenite stages of a knitted shape memory material according to the pattern of FIGS. 8A-8C, respectively.

FIG. 12A depicts a grid of graphical symbols of a pattern according to another embodiment.

FIGS. 12B and 12C depict martensite and austenite stages of a knitted shape memory material according to the embodiment of FIG. 12A, in straight and coiled states, respectively.

Figure 1A:
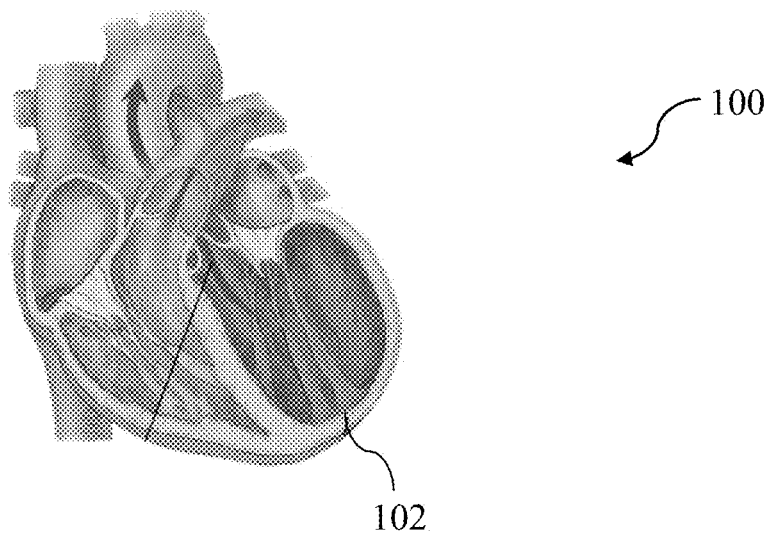
FIG. 1A is a simplified cross-sectional view of a heart.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

According to embodiments, devices are disclosed that can be used to provide support for a ventricle or other part of a cardiovascular system. Such devices can be tailored to have specific expanded and contracted states, or twisted and straight shapes or transitions there between, resulting from the orientation of various wires of shape memory material that make up the devices.

Knitting is a traditional textile manufacturing technique that creates a network of interlacing adjacent loops that form a three-dimensional structure. The loops can be assembled into different patterns to provide different mechanical properties.

In embodiments, devices can include knitted patterns of stitches such that the martensite and austenite stages of a knitted shape memory material correspond to two stages of the desired operation of the heart muscle against which they are arranged. For example, in one state the shape memory alloy can match the size and shape of the heart during diastole, whereas during the other stage the shape memory alloy can match the size and shape of the heart during systole.

In addition to simple expansion or contraction, such knitted patterns can be configured to twist, bend, or fold in particular ways during movement of the surrounding cardiovascular structures, in embodiments.

In further embodiments, the material that makes up the device need not be a shape memory alloy. Rather, the material can be any flexible material that is knitted into a pattern such that expansion or contraction of the overall device will cause a desired change to the overall superstructure of the device. For example, squeezing the device could cause the device to twist slightly, in embodiments, to match the twist to the surrounding ventricle, which prevents abrasion or damage to the surrounding cardiovascular structure.

Although embodiments are described herein that are knitted, similar devices could be made using other methods. For example, rather than by knitting, devices can be made using braiding, weaving, laser-cutting sheets or strands. Furthermore, additive manufacturing, three-dimensional printing, or other techniques can be used to generate meshes, knits, chain links, weaves, or other structures that will deform according to a desired plan. Using these or other methods, rows of a shape memory material or other substance having a predetermined level of expansion, spring constant, contraction, and/or twist can be produced.

FIG. 1A is a simplified cross-sectional view of a heart 100 having heart failure from reduced ejection fraction. In this condition, less blood is pumped out from the left ventricle than would be in a normal heart, due to a weakened heart muscle that is not capable of squeezing as well as a normal heart. As shown in FIG. 1A, left ventricle 102 delivers blood to the pulmonary artery, the lungs, and to the rest of the body as indicated by the arrows.

Figure 1B:
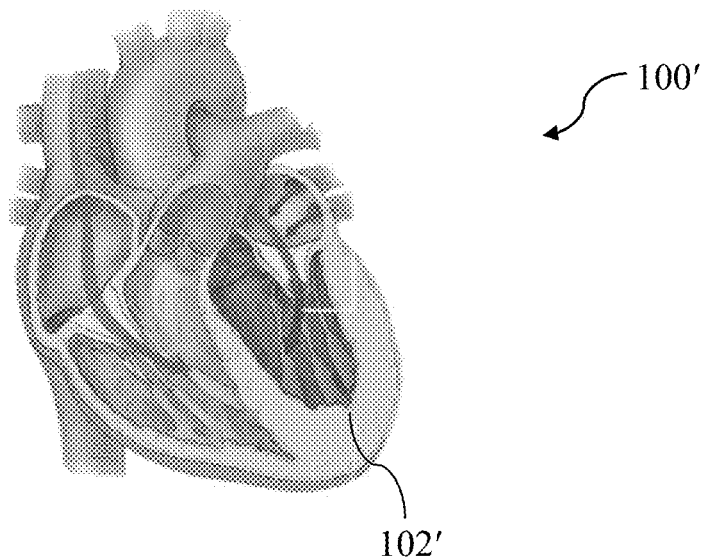
FIG. 1B is a simplified cross-sectional view of a heart suffering from heart failure with preserved ejection fraction (HFpEF).

FIG. 1B is a simplified cross-sectional view of a heart 100' suffering from heart failure with preserved ejection fraction (HFpEF). HFpEF causes less blood to flow to the left ventricle 102'. Often, a stiff heart does not relax normally, reducing this blood flow.

FIG. 1A depicts a heart 100 having a left ventricle 102 that is thinned and weak, and FIG. 1B depicts a heart 100' having a left ventricle 102' with a thick wall and reduced blood flow. In both of the hearts 100 and 100', a properly-sized left ventricle (102 or 102') would provide substantial benefits and improve cardiovascular function. While some pharmacological intervention is possible to treat heart failure reduced ejection fraction (as shown in FIG. 1A), no pharmacological treatments or devices are presently available to treat HFpEF (as shown in FIG. 1B).

Figures 2A, 2B:
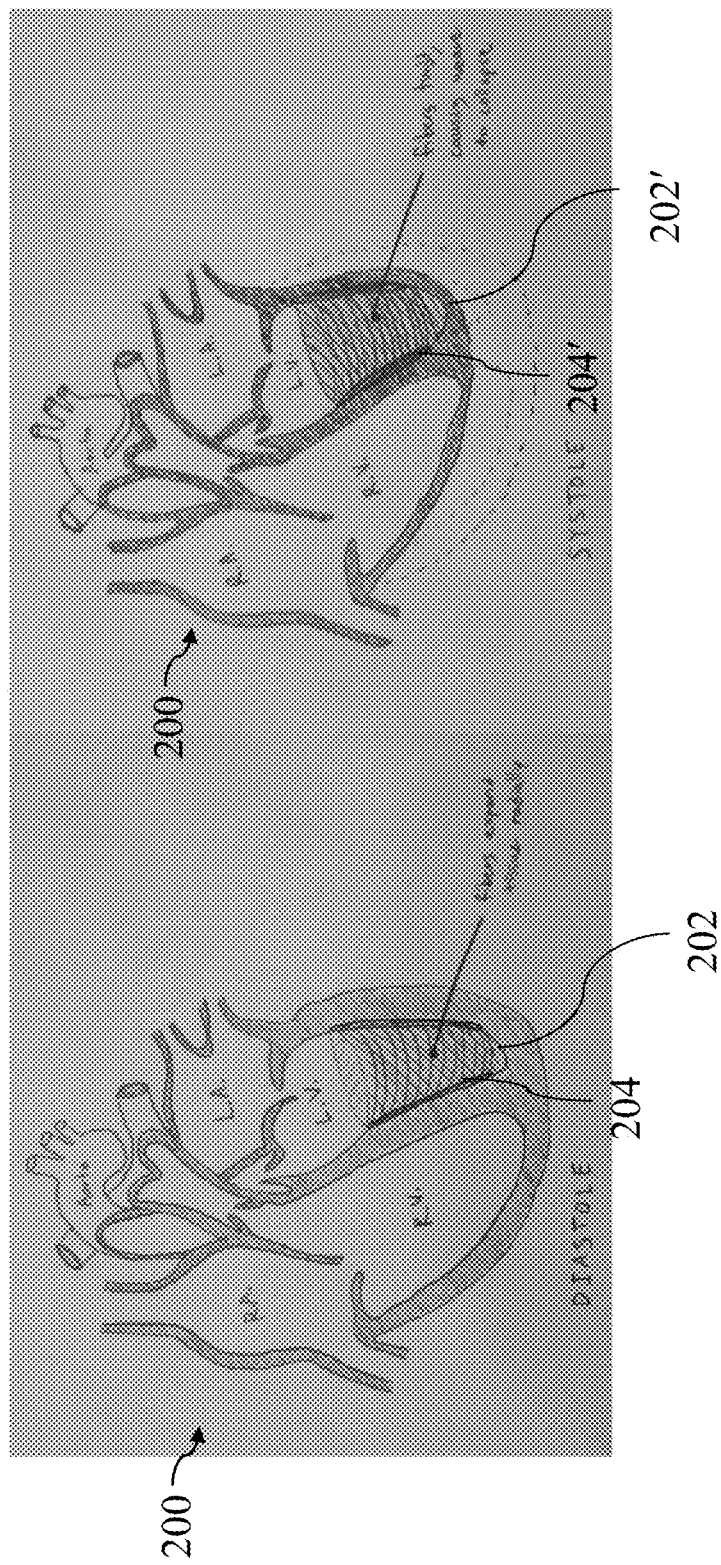
FIGS. 2A and 2B are simplified cross-sectional views of a heart having an expansible fiber mesh positioned in the left ventricle.

FIGS. 2A and 2B are simplified cross-sectional views of a heart having an expansible fiber mesh positioned in the left ventricle to treat HFpEF. FIG. 2A shows heart 200 in diastole, and uncompressed device 204 positioned therein. FIG. 2B shows the same heart 200 in systole, in which the left ventricle 202 of FIG. 2A is compressed (shown as 202' in FIG. 2B). FIGS. 2A and 2B further depict device 204 (in its uncompressed state) and 204' (in its compressed state), respectively.

In addition to mere radial compression, it can be desirable for device 204' to change in shape as it is compressed to the form shown in FIG. 2B. This change in shape can mirror the change in shape of the ventricle 202 in which it is positioned. In general, a left ventricle 202 undergoes both radial compression and an accompanying twisting motion along the longitudinal axis of the left ventricle 202 while changing from diastole to systole and back. Accordingly, as the compressed left ventricle 202' twists slightly along its length as compared to its uncompressed state 202, in order to prevent damage or abrasion to the left ventricle 202 as it compresses to 202' it is beneficial to provide a device 204 that will twist an approximately equivalent amount as it compresses to its own compressed state 204'.

In the embodiment shown in FIGS. 2A and 2B, the device (204 in diastole, 204' in systole) is made of a shape memory alloy. The shape memory can be activated to alternate between martensite and austenite to accompany the alternation of left ventricle (202, 202') between diastole and systole. In alternative embodiments, rather than a shape memory material, some other material could be used that will generate a similar twist or shape change upon compression. For example, in embodiments a material may be used which undergoes shape change under pressure due to, for example, a level of compressibility or spring constant. In embodiments, materials or combinations of materials can be used that undergo a desirable shape change upon compression based on one or more of these phenomena. In some embodiments, the knit configurations that make up device 204 (for example, the knitting patterns described below with respect to FIGS. 4-14) can be implemented to form a device 204 that will both contract and twist upon shape-memory transition based upon an expected level of contraction and twist of the left ventricle 202 as it goes between diastole and systole.

Figure 3A:
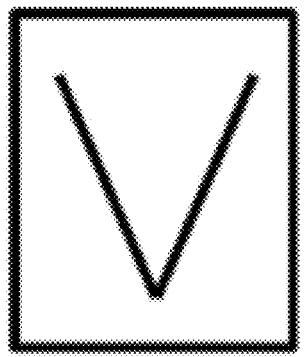
FIGS. 3A and 3B depict a graphical symbol for a knit loop and a top view of a knit loop, respectively.
Figure 3B:
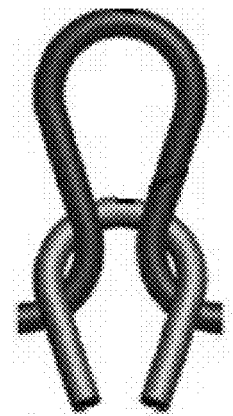
Figure 3C:
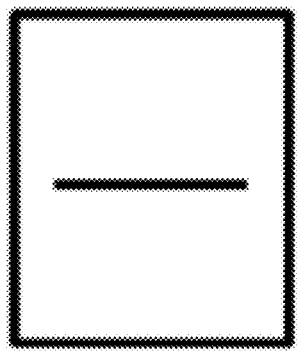
FIGS. 3C and 3D depict a graphical symbol for a knit loop and a top view of a purl loop, respectively.
Figure 3D:
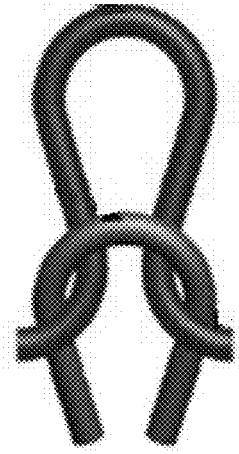

FIGS. 3A and 3B depict a graphical symbol for a knit loop and a top view of a knit loop, respectively. FIGS. 3C and 3D depict a graphical symbol of a purl loop and a top view of a purl loop, respectively. Various combinations of these and other knitted loops and patterns can be used to generate the desired level of twist described with respect to FIGS. 2A and 2B, for example. In alternative embodiments, other combinations of those and other knitted loops and patterns could be used to generate folds, kinks, pleats, and other desired shapes upon expansion or contraction of the structure.

Both the knit and purl loops are unit cells made up of a loop, two legs, and a ridge. The loop is curved slightly more than 180°, creating a tear-drop shape that forms the upper portion of the knit unit cell. The loop extends into the legs, where adjacent unit cells attach to one another. The ridge is the uppermost portion of the loop from the previous course (row); the intersecting ridge divides the loop from the legs. The feature that distinguishes between the loops is the location of the loop and legs with respect to the ridge. The knit loop is created by passing through the loop in the previous course from the back to the front and is characterized by a forward loop and a rear ridge. The legs of the knit loop interlock with the ridge, and then extend behind the ridge. Since the ridge is in the rear for knit loops only the base of the loop is visible; the base of the knit loop appears as a 'V' like shape on the textile and is represented in the symbolic grid with a 'V' of FIG. 3A (a standard notation in traditional knitting).

The purl loop (FIGS. 3C and 3D) is created by passing through the loop in the previous course from the front to the back and is characterized by a backward loop and a forward ridge. The legs of the purl loop interlock with the ridge, and then extend in front of the ridge. Because the ridge is in the front for purl loops it is visible; the ridge of the purl loop appears as a '-' like shape on the textile and is represented in the symbolic grid with a '-' (a standard notation in traditional knitting—shown in FIG. 3C). A purl loop on one side of the textile appears as a knit loop on the other side.

Throughout the remainder of this application, the "V" and "-" shapes are used in the figures as shorthand to indicate knit and purl loops, respectively.

Figure 4A:
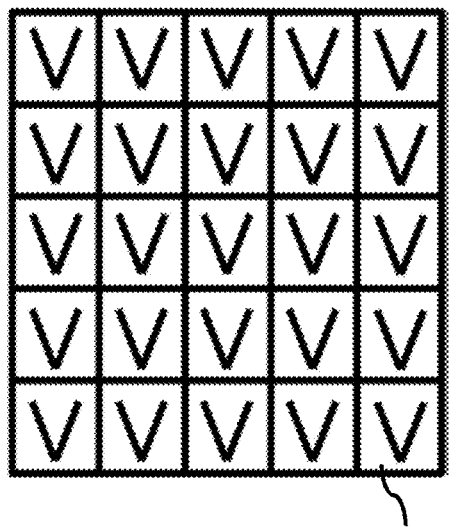
FIGS. 4A, 4B, and 4C depict a grid of graphical symbols of a pattern, a top view of the pattern, and a side view of the pattern, respectively.
Figure 4B:
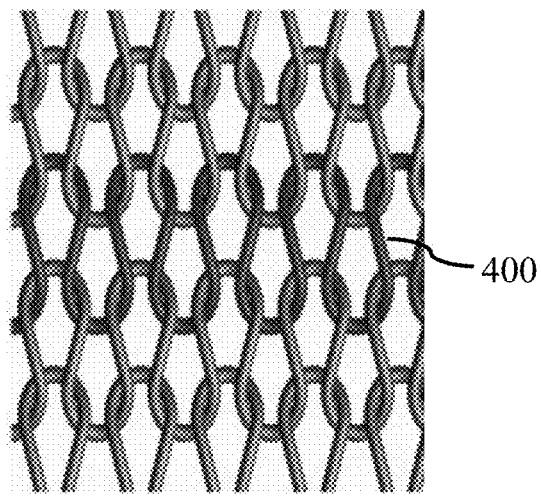
Figure 4C:
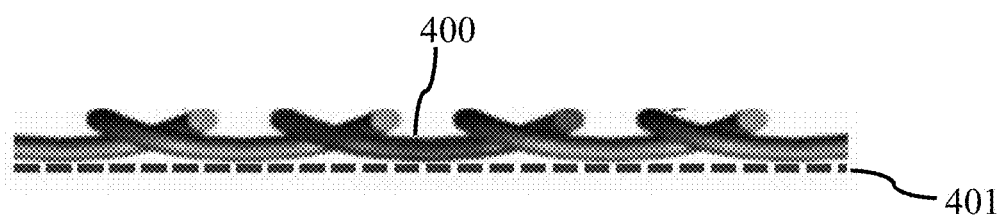

FIGS. 4A, 4B, and 4C depict a grid of graphical symbols of a pattern, a top view of the pattern, and a side view of the pattern, respectively. As shown in FIG. 4A, the pattern is entirely made of repeating rows of symbols indicating knit loops 400. FIG. 4B is a plan view of a corresponding knitted material made up of repeating rows of knit loops 400. FIG. 4C is a side view of the repeating rows of knit loops 400 previously described with respect to FIGS. 4A and 4B. As shown in FIG. 4C, the repeating rows of knit loops 400 present a smooth side 401, indicated by dashed lines.

FIGS. 4D and 4E depict the martensite stage of the knitted shape memory material according to the pattern described with respect to FIGS. 4A-4C. The knitting pattern of FIGS. 4A-4C is commonly referred to as stockinette. The rolling actuation motion of stockinette shown by the curling of device 402 into device 402' from FIG. 4D to FIG. 4E is driven by its asymmetric architecture. In embodiments of a device in which a rolling mechanism is desired, lengths of stockinette can be used to create that effect.

Figure 4F:
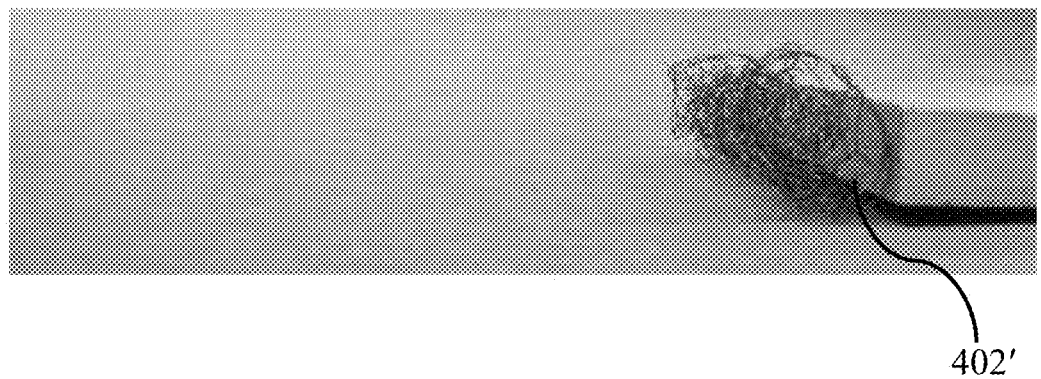
FIGS. 4F and 4G depict an austenite stage of the knitted shape memory material according to the pattern of FIGS. 4A-4C, respectively.
Figure 4G:
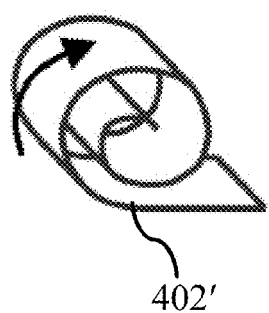

FIG. 4D is a photograph of the loose, unactivated shape memory material 402, which is a rectangular stockinette sheet 403 as shown in FIG. 4E. Upon activation, which can occur due to heat, electrical current, or any other actuating force depending on the material used to form device 402, the material transforms from one state to another. As shown in FIGS. 4F and 4G, the shape memory material has been transformed by undergoing a shape memory effect, causing device 402 of FIGS. 4D and 4E to curl into device 402' of FIG. 4F, and as depicted schematically by the arrow in FIG. 4G.

Figure 5A:
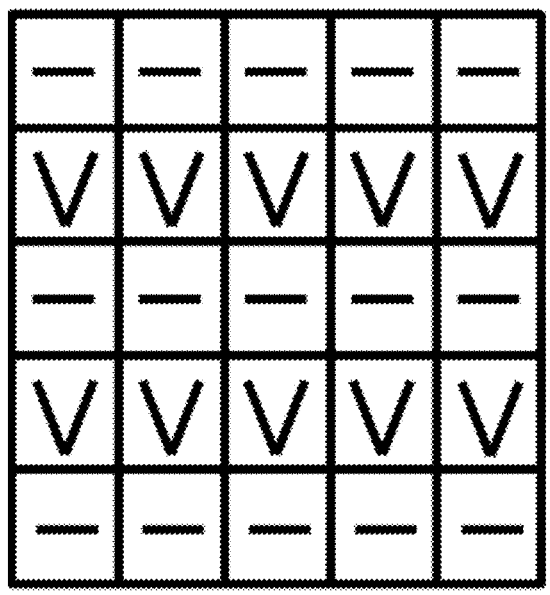
FIGS. 5A, 5B, and 5C depict a grid of graphical symbols of a pattern, a top view of the pattern, and a side view of the pattern, respectively.
Figure 5B:
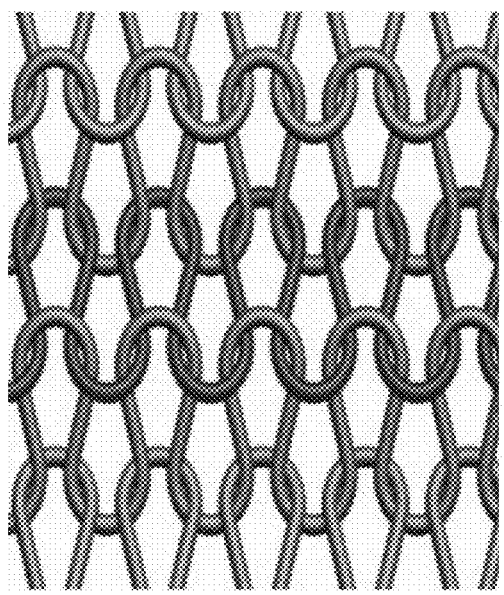
Figure 5C:

In comparison to the stockinette design shown in FIGS. 4A-4E, the design shown in FIGS. 5A-5E is a horizontally striped knit pattern, or garter. The pattern of the fabric is shown in FIG. 5A using the symbols described above for knit and purl loops. The distributed contraction of the garter 502 of FIG. 5D is driven by the alternating rows of knit and purl patterned shape memory wire as depicted in FIGS. 5A-5C. FIGS. 5A, 5B, and 5C depict a grid of graphical symbols of a pattern, a top view of the pattern, and a side view of the pattern, respectively. FIGS. 5D and 5E depict expanded garter 502 and contracted garter 502' stages of a knitted shape memory material according to the pattern described with respect to FIGS. 5A-5C.

FIG. 6A depicts a grid of graphical symbols of a welt pattern. FIGS. 6B and 6C depict an embodiment of a welt pattern knitted from a shape memory material. In particular, FIG. 6B shows a relaxed welt 602 in side view, whereas FIG. 6C shows a curled welt 602' in side view.

FIGS. 7A, 7B, and 7C depict a grid of graphical symbols of a vertically striped or ribbed knit pattern, a top view of the pattern, and a side view of the pattern, respectively. FIG. 7D depicts relaxed vertically striped knit device 702, whereas FIG. 7E depicts curled vertically striped knit device 702', according to the pattern described with respect to FIGS. 7A-7C.

FIGS. 8A-8C depict a grid of graphical symbols of a diagonally striped or seed stitch pattern, according to an embodiment. In particular, FIGS. 8A, 8B, and 8C depict a top view of the pattern, and a side view of the pattern, respectively. FIG. 8D depicts relaxed diagonally striped knit device 802, whereas FIG. 8E depicts curled diagonally striped knit device 802'. In embodiments, the spacing of the knit and purl stitches can be more widely spaced. For example, in one embodiment purl stitches can occur every 4 or 5 stitches.

In embodiments, the position of purl stitches can be arranged in rivers that are slanted with respect to the overall grid shown in FIG. 8A. That is, if purl stitches are arranged at stitch numbers n, 2n, 3n, 4n . . . in the first row, they may be arranged at n+1, 2n+1, 3n+1, 4n+1 . . . in the second row. In still further embodiments, there can be several contiguous rows in which the purl stitches are in the same stitch positions, before the stitch positions iterate. For example, four consecutive rows may have purl stitches in positions n, 2n, 3n, 4n, while the fifth through eighth arrange the purl stitches at positions n+1, 2n+1, 3n+1, 4n+1.

Additionally or alternatively, in embodiments there may be one or more rows containing no purl stitches, or one or more rows containing no knit stitches. For example, the first row may have purl stitches in positions n, 2n, 3n, 4n, the second through fourth rows may be entirely knit stitches (or entirely purl stitches), and the fifth row may contain purl stitches at positions n+1, 2n+1, 3n+1, 4n+1.

By selecting appropriate positions and number of purl stitches to place within surrounding knit stitches, the overall level of twist and contraction of the resultant knitted structure can be provided. The angle at which the rivers of purl stitches are arranged within the knit pattern affects the amount of twist that will result from changing the state of the shape memory alloy. Similarly, the ratio of purl to knit stitches in the pattern, as well as the presence or absence of rows or columns without any variety (i.e., all knit or all purl stitches) will affect the strength of the compression of the overall device 802 to 802'.

Figure 9A:
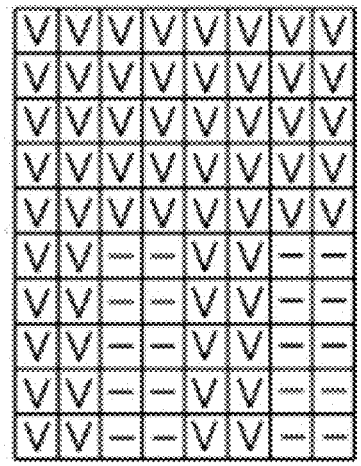
FIG. 9A depicts a grid of graphical symbols of a pattern.
Figure 9B:
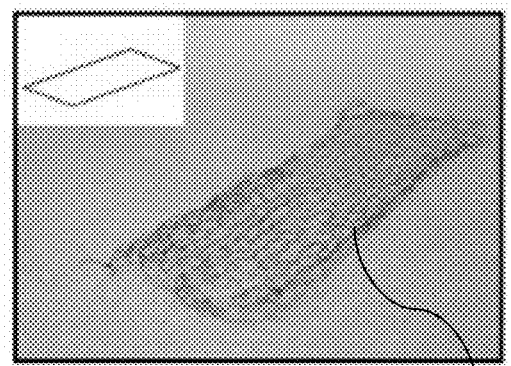
FIGS. 9B and 9C depict martensite and austenite stages of a knitted shape memory material according to the pattern of FIG. 9A, respectively.
Figure 9C:
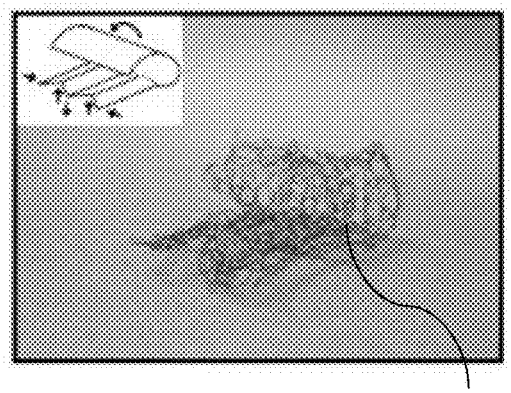

FIG. 9A depicts a grid of graphical symbols of a pattern configured to generate pleats, or ribbing. As shown in FIG. 9A, the rib knit portion comprises the bottom 5 rows of the table. The top five rows of FIG. 9A, in contrast, are stockinette. FIG. 9A therefore shows how a relaxed device 902 can therefore be made to form multiple connected structures when contracted as shown in FIG. 9C. Contracted device 902' as shown in FIG. 9C includes both a curled portion at the stockinette portion of the knit pattern of FIG. 9A, and also a pleated portion at the rib knit portion of the knit pattern of FIG. 9A.

Figure 10A:
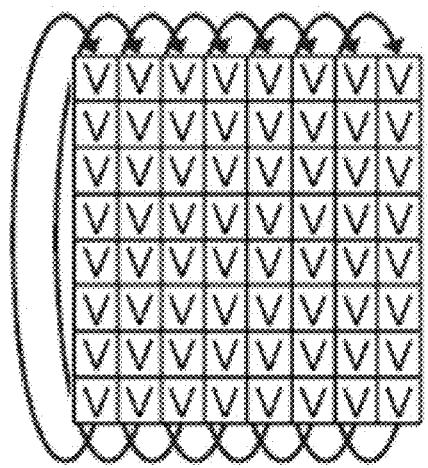
FIG. 10A depicts a grid of graphical symbols of a pattern according to an embodiment.
Figure 10B:
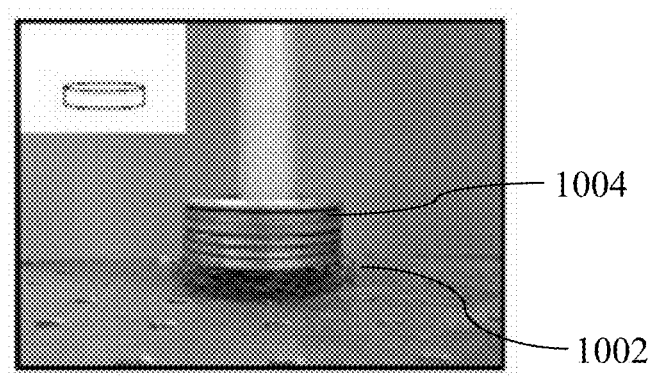
FIGS. 10B and 10C depict martensite and austenite stages of a knitted shape memory material according to the embodiment of FIG. 10A, in an expanded and contracted state, respectively.
Figure 10C:
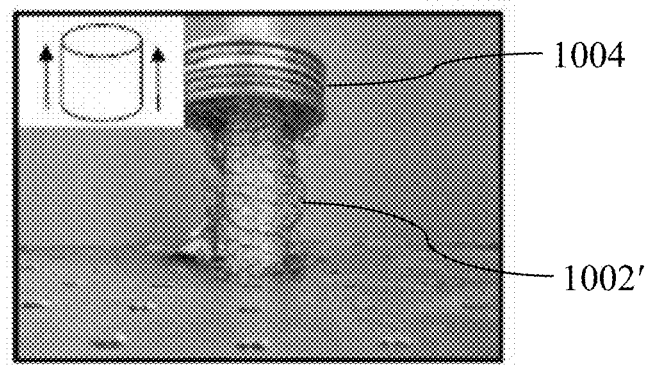

FIG. 10A depicts a grid of graphical symbols of a pattern according to an embodiment. In contrast to the other knit patterns shown and described above, the knit pattern shown in FIG. 10A is circularized and forms a full cylindrical loop. FIGS. 10B and 10C depict martensite and austenite stages of a knitted shape memory material according to the embodiment of FIG. 10A, in an compact and expanded states 1002 and 1002', respectively. FIGS. 10B and 10C show how activation of a knitted pattern can provide force to, for example, lift weight 1004. Similarly, in embodiments a shape memory alloy knitted mesh could be used to apply force to the wall of a heart ventricle, for example.

Figure 11A:
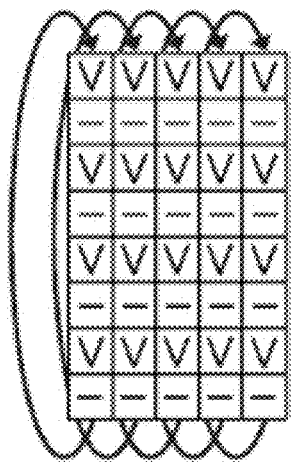
FIG. 11A depicts a grid of graphical symbols of a pattern according to another embodiment.
Figure 11B:
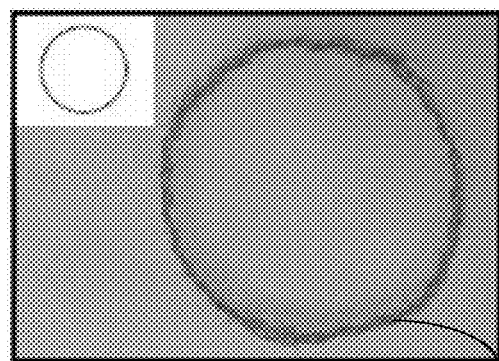
FIGS. 11B and 11C depict martensite and austenite stages of a knitted shape memory material according to the embodiment of FIG. 11A, in an expanded and contracted state, respectively.
Figure 11C:
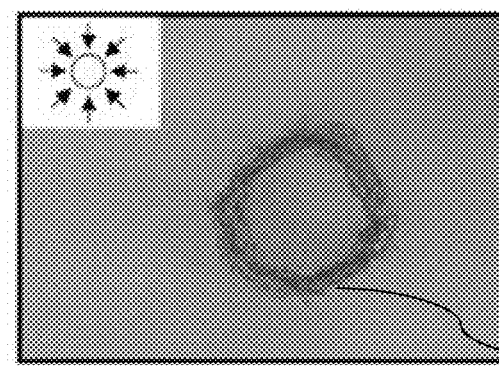

FIG. 11A depicts a grid of graphical symbols of a pattern according to another embodiment. As compared to the embodiment of FIG. 10A, the knit pattern includes alternating knit and purl stitches. FIGS. 11B and 11C depict relaxed and contracted stages 1102 and 1102' of a knitted shape memory material device according to the embodiment of FIG. 11A.

FIG. 12A depicts a grid of graphical symbols of a pattern according to another embodiment. FIGS. 12B and 12C depict martensite and austenite stages of a knitted shape memory material according to the embodiment of FIG. 12A, in straight and coiled states, respectively. FIGS. 12A-12C depict course-wise restructuring such as that used to generate I-cord textiles. As shown in FIGS. 12A-12C, courses of a stockinette grid pattern can be restructured by helically knitting across the textile to form a knitted tube which actuate from device 1102, a thin long tube, into device 1102', a helically coiled structure in austenite state. Course-wise restructuring forms restructured grids that can produces novel out-of-plane actuation behavior.

Figure 13A:
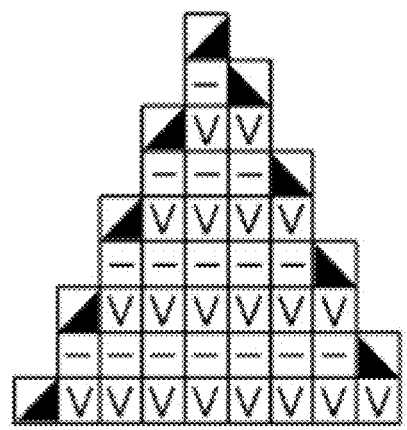
FIG. 13A depicts a grid of graphical symbols of a pattern according to an embodiment.
Figure 13B:
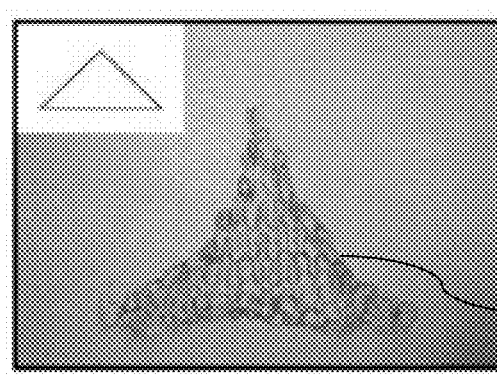
FIGS. 13B and 13C depict martensite and austenite stages of a knitted shape memory material according to the embodiment of FIG. 13A, respectively.
Figure 13C:
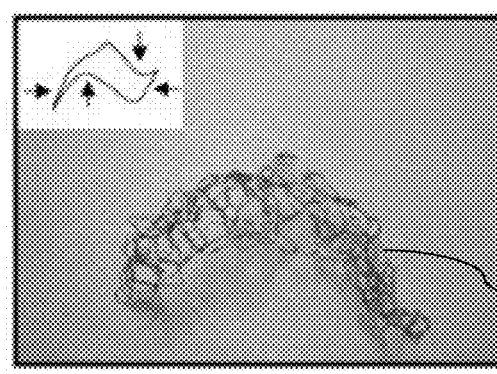

FIG. 13A depicts a grid of graphical symbols of a pattern. In particular, in addition to knit and purl identifiers, FIG. 13 also includes indications to merge (i.e., "knit together" or "purl together") adjacent stitches in alternating courses to form a triangularly shaped actuator 1302 as shown in FIG. 13B. Actuation of the memory shape alloy causes the structure to deform to become contracted triangle device 1302'. The curl is in opposite directions at each edge due to the asymmetric boundary conditions in the austenite state.

Figure 14A:
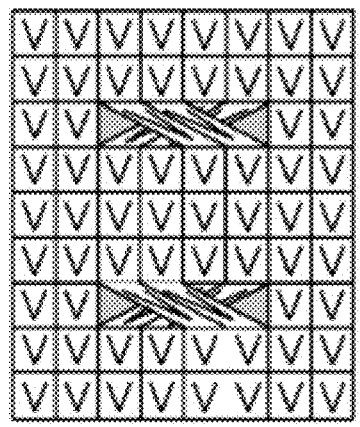
FIG. 14A depicts a grid of graphical symbols of a pattern according to another embodiment.
Figure 14B:
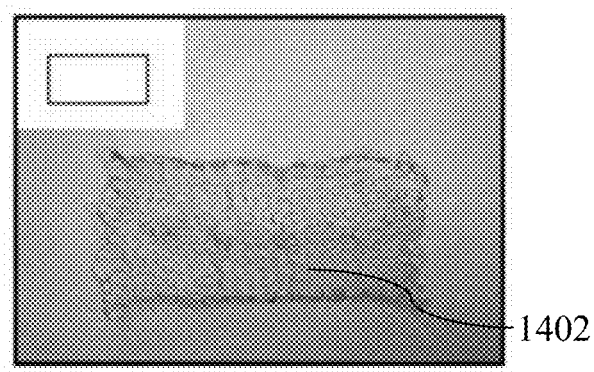
FIGS. 14B and 14C depict martensite and austenite stages of a knitted shape memory material according to the embodiment of FIG. 12A, in flat and folded states, respectively.
Figure 14C:
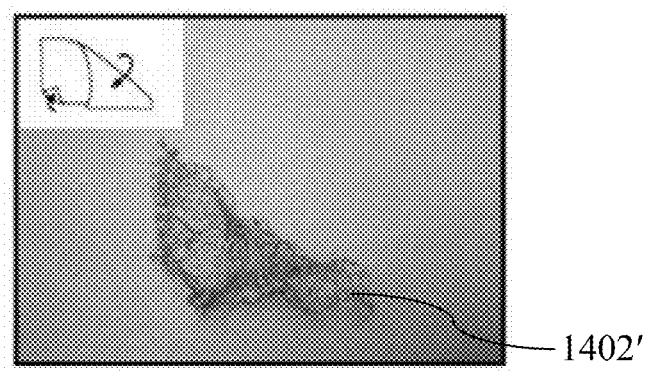

FIG. 14A depicts a grid of graphical symbols of a pattern according to another embodiment having a restructure grid. In particular, FIG. 14A shows a re-ordered grid similar to that used to make cables in a knitted textile. FIGS. 14B and 14C depict martensite and austenite stages 1402 and 1402' of a knitted shape memory material according to the embodiment of FIG. 14A. As shown in FIG. 14C, the device 1402' is torque along its length in the austenite state. Re-ordering the grid creates new motions during activation of the shape memory material that are unavailable with knit patterns alone.

Figure 15:
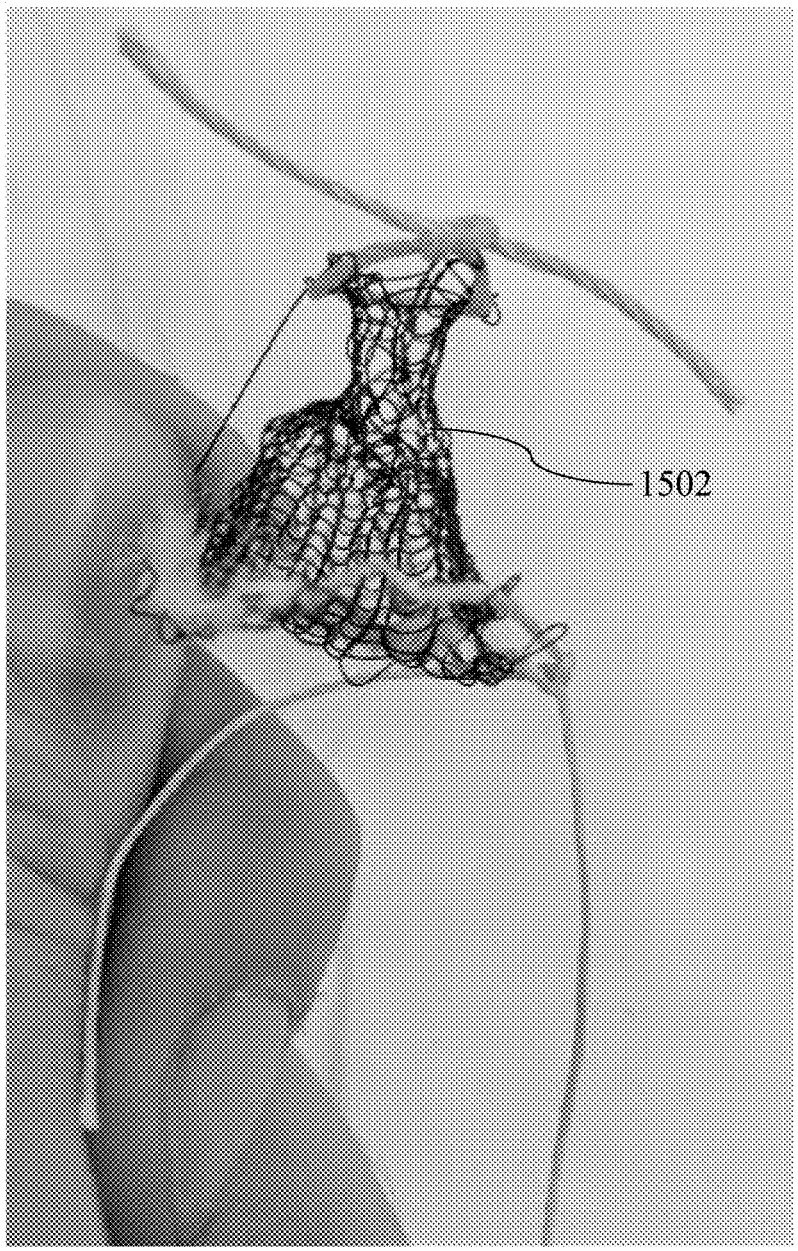
FIG. 15 is an implantable knitted device according to an embodiment.

FIG. 15 depicts a knitted device 1502 that can be implanted into a cardiovascular system. For example, the device 1502 shown in FIG. 15 could be implanted into a ventricle of the heart in order to treat HFpEF. Device 1500 is capable of superelastic expansion in three dimensions, and is made of a superelastic shape memory material. In embodiments device 1502 can aid in the expansion of the left ventricle, as depicted previously with respect to FIGS. 2A and 2B, by providing a radially outward restoring force on the interior wall of the left ventricle. The expansion force increases the volume of the left ventricle, which improves filling while reducing the pressure in the left ventricle.

Device 1502 is an implantable knitted basket according to an embodiment. As shown in FIG. 15, device 1502 is sized approximately to match the size of a left ventricle. Furthermore, in a compressed state, device 1502 can be delivered to the left ventricle via a catheter, rather than via more invasive surgical techniques. In some embodiments, for example when open-heart surgery is required to treat other conditions, device 1502 could be positioned directly in the left ventricle rather than being provided by a catheter. By positioning device 1502 without the aid of a catheter, device 1502 can be formed in an uncompressed state (e.g., martensite).

Device 1502 can expand the left ventricle when positioned therein. This increases both the diameter of the left ventricle, and also the volume of the left ventricle. Device 1502 has elasticity and can improve stroke volume of the heart and cardiac output. Device 1502 is capable of anchoring to stay in place, reducing systolic inefficiency and flow disruption. Impact on the ventricle is minimized because device 1502 can twist, fold, or otherwise modify its shape with each stroke to match the movement of the inner wall of the ventricle.

The unique mechanical properties of device 1502 are enabled by the combination of the superelastic material and textile manufacturing process or knitting of device 1502. Device 1502 can be manufactured with a superelastic material, such as nitinol, and in embodiments can have shape memory attributes. Nitinol is well known in the field of medical devices because it is biocompatible and can be approved for long term device implantation. Additionally, because nitinol is superelastic, it can undergo large recoverable materials strains on the order of 2-8% in embodiments. The extreme elasticity of nitinol enables it to be incorporated into a knitted structure.

Device 1502 is a helically knit three-dimensional tube or basket. Device 1502 is manufactured using a basic knit pattern with 0.012" nitinol wire to form a flexible cylinder with a 1" diameter and 2" length, in the embodiment shown in FIG. 15, but in other embodiments it could be larger, smaller, or have various other shapes such as those including the features shown previously with respect to FIGS. 4-14. The geometric properties of each embodiment can be tailored to obtain a desired mechanical performance as well.

Changes to the knit pattern can enable compression for delivery. For example, device 1502 or similar embodiments can be compressible such that they can be delivered to a desired portion of a cardiovascular system via a catheter or other non-invasive delivery technique.

Stockinette, garter, welt, rib, seed, and grid knitting techniques, as described with respect to FIGS. 4-9, respectively, can be incorporated into an overall basket pattern according to embodiments of the device. While various examples of knitted stitches and patterns of knitted stitches have been provided herein, other stitches and patterns of stitches can be used in other embodiments. For example, yarn-overs and other methods of adding stitches to rows ("increases") can also be incorporated. Similarly, methods of reducing or combining stitches other than knitting two stitches together or purling two stitches together also can be used. Moreover, crocheting and other needlework techniques also can be used in embodiments to achieve particular desired effects, patterns and/or behaviors of materials. In still other embodiments, multiple materials and/or multiple strands of materials also can be used in the knitted or otherwise formed material.

In one embodiment, a manufacturing method comprises forming a first row of stitches of a shape memory material. The method further comprises forming a plurality of subsequent rows of stitches of a shape memory material coupled to the first row to form a device, wherein each of the plurality of subsequent rows comprises stitches selected to implement a predetermined level of contraction and twist of the device. Forming the first row and the subsequent rows includes one of the group consisting of stitching, knitting, braiding, laser cutting, and additive manufacturing.

In embodiments, the manufacturing method can alternatively or additionally include forming a plurality of subsequent rows of a shape memory material coupled to the first row to form a device, wherein each of the plurality of subsequent rows selected to implement a predetermined level of expansion of the device. Additionally and/or alternatively, the manufacturing method can include forming a plurality of subsequent rows of a shape memory material coupled to the first row to form a device, wherein each of the plurality of subsequent rows selected to implement a predetermined spring constant of the device.

According to another embodiment, a delivery method comprises providing a device having a plurality of rows of a shape memory material configured to implement a predetermined level of contraction and twist, contracting the device within a catheter system, delivering the device via the catheter system to a portion of a patient's cardiovascular system, and expanding the device to support the portion of the patient's cardiovascular system.

According to yet another embodiment, a device comprises a plurality of knitted rows of a shape memory material configured to implement a predetermined level of expansion, spring constant, contraction, and/or twist.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A medical device comprising:
a plurality of interconnected loops of a superelastic material that define a basket, each of the plurality of interconnected loops arranged in one of a knit pattern or a purl pattern,
wherein the basket is configured to have two, expanded state, shape-memory orientations, and wherein the basket is configured to both contract and twist upon shape-memory transition between the two, expanded state, shape-memory orientations, and
wherein the medical device is configured to be implanted within a body of a patient.

2. The device of claim 1, wherein the basket comprises a stockinette portion defined by a subset of the plurality of interconnected loops of the superelastic material.

3. The device of claim 1, wherein the basket comprises a garter portion defined by a subset of the plurality of interconnected loops of the superelastic material.

4. The device of claim 1, wherein the basket comprises a welt portion defined by a subset of the plurality of interconnected loops of the superelastic material.

5. The device of claim 1, wherein the basket comprises a seed portion defined by a subset of the plurality of interconnected loops of the superelastic material.

6. The device of claim 1, wherein the basket comprises a rib portion defined by a subset of the plurality of interconnected loops of the superelastic material.

7. The device of claim 1, wherein the basket comprises a grid portion defined by a subset of the plurality of interconnected loops of the superelastic material.

8. The device of claim 1, wherein the basket is configured to both contract and twist upon shape-memory transition based upon an expected level of contraction and twist of a left ventricle of a human heart.

9. The device of claim 1, wherein, in a compressed state, the device can be delivered to a left ventricle of a human heart via a catheter.

10. A method for treating a heart exhibiting heart failure with preserved ejection fraction, the method comprising:
forming a medical device by interconnecting a plurality of loops of a superelastic material to define a basket, each of the plurality of interconnected loops arranged in one of a knit pattern and a purl pattern, wherein the basket is configured to have two, expanded state, shape-memory orientations, and wherein the basket is configured to both contract and twist upon shape-memory transition between the two, expanded state, shape-memory orientations, and wherein the medical device is configured to be implanted within a body of a patient; and
providing the formed device.

11. The method of claim 10, wherein:
forming the device comprises forming the device into a compressed state; and
providing the formed device comprises positioning the device in the compressed state in a catheter.

12. The method of claim 10, wherein forming the device comprises forming a stockinette portion defined by a subset of the plurality of interconnected loops of the superelastic material.

13. The method of claim 10, wherein forming the device comprises forming a garter portion defined by a subset of the plurality of interconnected loops of the superelastic material.

14. The method of claim 10, wherein forming the device comprises forming a welt portion defined by a subset of the plurality of interconnected loops of the superelastic material.

15. The method of claim 10, wherein forming the device comprises forming a seed portion defined by a subset of the plurality of interconnected loops of the superelastic material.

16. The method of claim 10, wherein forming the device comprises forming a rib portion defined by a subset of the plurality of interconnected loops of the superelastic material.

17. The method of claim 10, wherein forming the device comprises forming a grid portion defined by a subset of the plurality of interconnected loops of the superelastic material.

18. A method comprising:
providing a device having a plurality of interconnected loops of a superelastic material that define a basket, each of the plurality of interconnected loops arranged in one of a knit pattern and a purl pattern;
delivering the device in a compressed state via catheter to a left ventricle of a heart; and
expanding the device from the compressed state to an at least partially expanded state at the left ventricle, wherein the basket is configured to transition between two, expanded state, shape-memory orientations, wherein the basket both contracts and twists upon shape-memory transition between the two, expanded state, shape-memory orientations.

19. The method of claim 18, further comprising actuating the superelastic material in coordination with the transition between diastole and systole of the heart such that the basket undergoes contraction and twisting corresponding to a contraction and twist of a left ventricle.

20. The device of claim 1, wherein the basket upon shape-memory transition between the two, expanded state, shape-memory orientation is configured to transition between a first shape that substantially conforms to a ventricle shape during diastole of a heart and a second shape that substantially conforms to a ventricle shape during systole of the heart.

21. The device of claim 1, wherein the basket is configured to be collapsed to a compressed state that is deliverable by a catheter, wherein the compressed state is different than the two, expanded state, shape-memory orientations.

* * * * *